United States Patent [19]

Székely et al.

[11] Patent Number: 4,479,945
[45] Date of Patent: Oct. 30, 1984

[54] INTER-M-PHENYLENE-PROSTACYCLIN ANALOGUES AND USE THEREOF IN INHIBITING BLOOD PLATELET AGGREGATION

[75] Inventors: István Székely, Dunakeszi; Sádor Botá; Marianna G. Lovász, both of Budapest; Krisztina K. Dolgos, Debrecen; Gábor Kovács, Budapest; Sándor Virág, Budapest; Tamás Szüts, Budapest; Istvá Rákóczi, Budapest; Károly Tihanyi, Budapest; Péter Körmöczy, Budapest; Pál Hadházy, Budapest; Istvá Stadler, Budapest; György Blaskó, Budapest; Béla Köszegi, Budapest, all of Hungary

[73] Assignee: Chinoin Gyogyszer Es Vegyeszeti Termekek Gyara R.T., Budapest, Hungary

[21] Appl. No.: 445,044

[22] Filed: Nov. 29, 1982

[30] Foreign Application Priority Data

Dec. 1, 1981 [HU] Hungary ............................. 3600/81
Oct. 22, 1982 [HU] Hungary ............................. 3378/82

[51] Int. Cl.³ .................. A61K 31/34; C07D 307/935
[52] U.S. Cl. ..................................... 424/184; 424/283; 424/285; 424/308; 424/317; 542/426; 542/429; 542/430; 560/56; 562/466; 556/441; 549/378; 549/414; 549/465
[58] Field of Search ...................... 549/415, 421, 422; 542/426, 429, 430; 560/56; 562/466; 424/285, 308, 317, 283, 184

[56] References Cited

U.S. PATENT DOCUMENTS 4,306,076 12/1981 Nelson ............................... 546/309
4,372,971 2/1983 Seipp ................................... 424/285

FOREIGN PATENT DOCUMENTS 62902 4/1982 European Pat. Off. .

Primary Examiner—John M. Ford
Assistant Examiner—Bernard Dentz
Attorney, Agent, or Firm—Karl F. Ross; Herbert Dubno

[57] ABSTRACT

New inter-m-phenylene-PGI₂ derivatives are prepared of the general formula I

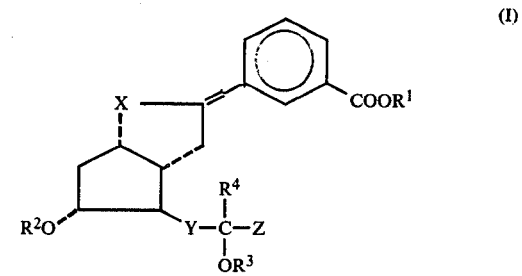

wherein
R¹ stands for hydrogen, alkyl containing 1 to 4 carbon atoms or a pharmaceutically acceptable primary, secondary, tertiary or quaternary ammonium cation or a metal cation,
R² and R³ stand independently on each other for hydrogen, alkanoly, aroyl or an acetal type or alkyl silyl type protecting group,
R⁴ represents hydrogen or an alkyl group containing 1 to 4 carbon atoms,
X stands for oxygen, or a—CH₂—group,
Y stands for—C≡C— or a trans—CH=CW group, wherein W stands for chlorine, bromine or fluorine,
Z represents an alkyl group having 6 to 9 carbon atoms, optionally substituted by one or more alkyl groups containing 1 to 4 carbon atoms or fluorine or it stands for an optionally substituted arylmethyl or aryloxy methyl group.

The new compounds are active ingredients of pharmaceutical compositions having antiaggregatory activity.

16 Claims, No Drawings

INTER-M-PHENYLENE-PROSTACYCLIN ANALOGUES AND USE THEREOF IN INHIBITING BLOOD PLATELET AGGREGATION

The present invention relates to new inter-m-phenylene-prostacycline analogues and process for the preparation thereof.

The invention further relates to pharmaceutical compositions mainly of blood platelet antiaggregatory activity containing as active ingredient the new compounds.

The new inter-m-phenylene-prostacycline analogues can be characterized by the formula I

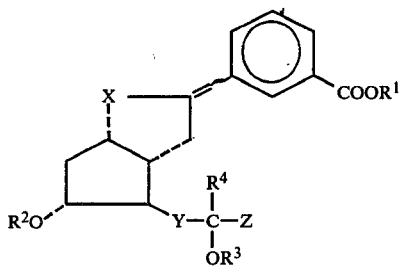

wherein
R$^1$ stands for hydrogen, alkyl containing 1 to 4 carbon atoms, or a pharmaceutically acceptable primary, secondary, tertiary or quaternary ammonium cation or a metal cation,
R$^2$ and R$^3$ are independently of each other hydrogen, alkanoyl, aroyl or an acetal type or alkylsilyl type protecting group,
R$^4$ stands for hydrogen or alkyl containing 1 to 4 carbon atoms,
X stands for oxygen or a —CH$_2$— group,
Y represents —C≡C— or CH=CW wherein W represents chlorine, bromine or fluorine,
Z stands for an alkyl group containing 6 to 9 carbon atoms, optionally substituted by one or more fluorine or alkyl containing 1 to 4 carbon atoms or for an optionally substituted arylmethyl or aryloxymethyl group.

The compounds according to the invention exhibit valuable antiaggregatory activity which is comparable with the same activity of PGI$_2$, and possess a hypotensive activity being by orders of magnitude lower than PGI$_2$, i.e. the activity-selectivity of the new compounds is by orders of magnitude higher, and the stability thereof is also higher than that of PGI$_2$. Thus the compounds can be used in the human and veterinary therapy for inhibiting or controlling blood clotting and as thrombolytic agents.

Prostacycline (PGI$_2$) was first disclosed in 1976 [Nature, 1976, 263 and 663; Prostaglandins, 1976, 12, 915; Angew. Chem. Int. Ed. Engl. 1978, 17, 293].

It was found that prostacycline is the most active antiaggregatory and desaggregatory agent and possesses further physiological activities, such as relaxation of the coronary arteries of the heart and dilatation of the peripheral circulation vessels. Since the discovery of prostacycline an intensive search has been carried out to synthetize compounds the anti- and desaggregatory activity of which would come close to that of prostacycline being simultaneously more stable chemically than the natural substance and the activity of which is more selective, than the activity of prostacycline and their metabolism is inhibited in the direction of the known main metabolism.

In DOS No. 29 45 781 prostacycline analogues have been disclosed which contain an o-phenylene group in the side chain bearing a carboxylic group. The compounds are disclosed to have a broad spectrum of activity and to be suitable for stimulating the smooth muscle at a dosage of 0.01–50 μg/kg body weight/min. administered intravenously, for controlling the thrombocyte aggregation at a dosage of 0.01–10 mg./kg. body weight administered intravenously, for decreasing blood pressure at a dosage of 0.01–50 μg./kg. body weight/min. administered intravenously, for reducing gastric acid secretion at a dosage of 0.1–20 μg./kg. body weight/min. administered intravenously, for the treatment of gastro-intestinal disorders caused by non-steroidal antiinflammatory agents at an indefinite dosage, for bronchodilatation (anti-asthmatic activity) at an oral dosage of 0.01–5 mg./kg. and for the treatment of various dermatosis at an indefinite dosage. The above list shows that as a consequence of the prostacycline structure modified as given in the above DOS, the end products show simultaneously several activities. Apart from the desired main activity all the other activities have to be considered as being undesired side-effects, i.e. a disadvantage in the therapy, as these side-effects can occur during the therapy and further drug-treatment is then required against these side-effects.

In European Patent Publication No. 0 045 842 Patent Application No. 81104982.4 PGI$_2$-analogues containing m-phenylene in the side chain bearing the carboxylic group are disclosed. As an advantage of the end products the narrower spectrum of activity compared with 5,6-dihydro-prostacycline and the better selectivity in the field of the antihypertensive side-effect compared to the same 5,6-dihydro-prostacycline is mentioned. The higher stability related to the prostacycline is emphasized. According to the published European application the compounds bear ethylene, vinylene or —C≡C— group in 13,14-positon, and the 16,20 alkyl group is replaced by pentyl optionally mono- or disubstituted in position 1 or by cyclohexyl optionally substituted in position 4.

The compounds may optionally be substituted by a methyl group in position 15 as well.

Substantially similar compounds are disclosed in the European Patent Publication No. 0062902 (Patent Application No. 82103024.4). These end-products differ from PGI$_2$ in containing m-phenylene in the side chain bearing the carboxylic group and containing in the lower side chain in position 20 a methyl or ethyl group or containing instead of the 16,20 side chain a phenoxymethyl, m-trifluoromethyl-phenoxymethyl group, or a 1-(optionally substituted)-amino-(C$_{4-6}$)alkyl- or phenyl- or benzyl group. The antiaggregatory activity according to the published specification is lower (by one order of magnitude) than that of PGI$_2$ though a significant advantage is the 1/50-1/80 activity in the field of antihypertensive activity compared with PGI$_2$ and that its stability exceeds the stability of PGI$_2$ considerably.

We have now found that the desired blood platelet antiaggregatory activity could be further increased and the undesired antihypertensive activity could be further reduced by using the new compounds according to the invention. At the same time the stability of the compounds is also maintained.

Comparative tests were carried out to compare antiaggregatory and antihypertensive activity.

As test-substances the following compounds were used: the known $PGI_2$, 5(Z)-2,3,4-trinor-1,5-inter-m-phenylene-$PGI_2$ (hereinafter referred to as 45842/A), 5(Z)-2,3,4-trinor-1,5-inter-m-phenylene-20-methyl-$PGI_2$ (hereinafter referred to as 62902), 5(Z)-2,3,4-trinor-1,5-inter-m-phenylene-13,14-didehydro-$PGI_2$ (referred to hereinafter as 45842/B), 5(Z)-2,3,4-trinor-1,5-inter-m-phenylene-13,14-didehydro-20-methyl-$PGI_2$ (referred to hereinafter as compound "A") and 5(Z)-2,3,4-trinor-inter-m-phenylene-13,14-didehydro-20-ethyl-$PGI_2$ (referred to hereinafter as compound "B") in the form of their sodium salts.

The thrombocyte aggregation was measured with a Payton type aggregometer of two channels in 0.5 ml. end volume. The necessary amount of blood was taken from such persons who had previously not taken any agent influencing thrombocyte aggregation for two weeks and did not suffer in kidney or liver disease. The cubital venal blood was mixed with a 3.8% Na-citrate solution at a ratio of 9:1 and in order to obtain a plasma enriched in thrombocytes (PRP) blood was centrifuged for 5 minutes at 230 g, while plasma poor in thrombocytes was obtained after 10 minutes of centrifuging. The blood platelet number of the plasma was adjusted to $2-3\times 10^5$/ml. The tests were performed within 1 hour after the blood taking. The prostacycline sensitivity of each plasma was controlled before measuring the test substances. $IC_{50}$ value of prostacycline on plasma enriched in thrombocytes: 0.6–1.0 ng/ml.

Thrombocyte aggregation was induced with 2 $\mu M$ ADP. The test compounds were dissolved in 0.1M tris-HCl buffer of pH=7.8 and the temperature was maintained at 0° to 4° C.

The compounds were tested repeatedly after some time and were kept in solution at 0°–4° C. $IC_{50}$ values were calculated graphically.

The antihypertensive activity was determined on narcotized rats. From the data of the blood pressure tests the molar dose /$ED_{25}$/ inducing 25 mmHg /3.33 kPa/ blood pressure reduction was calculated.

The antiaggregatory and antihypertensive efficacy related to $PGI_2$ is given in the following Table.

TABLE

| Test substance | relative anti-aggregatory efficiency $IC_{50}PGI_2/IC_{50}$ test-compound | relative anti-hypertensive efficiency $ED_{25}PGI_2/ED_{25}$ test-compound |
|---|---|---|
| $PGI_2$ | 1/1 | 1/1 |
| 45842/A | 1/50–1/70 | 1/10 |
| 45842/B | 1/20–1/30 | 1/20–1/30 |
| 62902 | 1/15–1/20 | 1/50–1/80 |
| compound "A" | 1/2–1/4 | 1/100–1/150 |
| compound "B" | 1/1–1/2 | 1/200–1/230 |

The table unambiguously shows that compounds "A" and "B" exhibit a better activity and less side effects than the compounds according to the state of art. Compound "B" is particularly important as its useful antiaggregatory activity is substantially the same as that of $PGI_2$ whereas the undesired side-effect, i.e., the antihypertensive activity of the compound is about 2/100 part of the activity of $PGI_2$. The stability of the end-products of the invention is characterized by having a several days long half-life even in strong acidic medium (pH=1), thus they can be prepared as compositions suitable for oral administration. Apart from the higher chemical stability and strong antiaggregatory and desaggregatory activity a further advantageous property of the compounds according to the invention is the several times longer duration of activity thereof compared with prostacycline. The metabolism of the natural prostaglandins is very rapid. The metabolism products where determined by physico-chemical methods and it was found that the metabolism consists of the chemical hydrolysis, or the beta-oxydation of the upper chain or oxydation of the 15-hydroxy group to 15-keto group.

These metabolism routes are inhibited in case of the compounds according to the invention. The aromatic ring built in to the so called upper chain eliminates the aliphatic beta-oxydation. From the point of view of the activity the critical chain length does not change even in case of various metabolistic reactions of the phenyl group, such as hydroxylation.

The oxydation of the 15-hydroxyl group is carried out by the so called 15-hydroxy-prostaglandine dehydrogenase (PGDH) enzyme system. It is known from the chemistry of the natural prostaglandins that by certain structural modifications the compounds are not substrates of the PGDH enzyme system, thus the inactivation process does not occur.

In order to examine the duration of activity the "ex vivo" method was used on rabbit test animals. The duration of antiaggregatory activity is 5–10 times longer than that of prostacycline.

According to the invention the compounds of the formula I

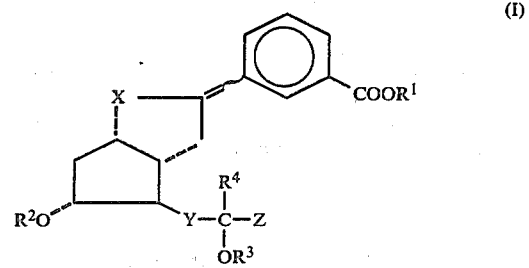
(I)

can be prepared by
(a) reacting lactols of the general formula II

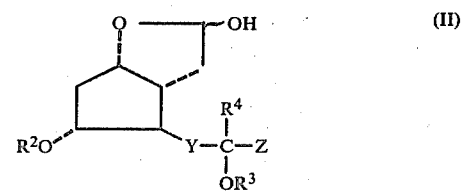
(II)

with phosphorans of the general formula IX

(IX)

wherein Ph is phenyl and reacting the obtained $PGF_2$-derivative of the general formula IV

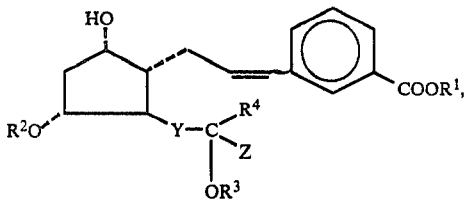

(IV)

with an electrophilic agent of the general formula E-L, wherein L stands for halogen or 2,5-dioxo-pyrrolidine-1-yl and E stands for halogen, phenyl-selenyl, phenyl-sulfenyl or E-L stands for pyridinium bromide-per-bromide or N-halogen-hydantoine, subjecting the obtained 5-substituted-PGI$_1$-derivative of the general formula V

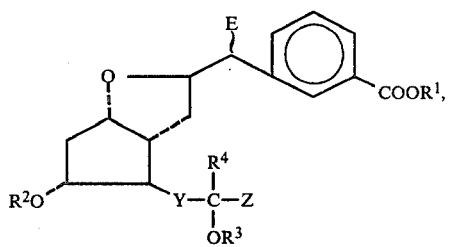

(V)

to elimination in order to prepare compounds of the general formula I, wherein X stands for oxygen, or (b) reacting a ketone of the general formula III

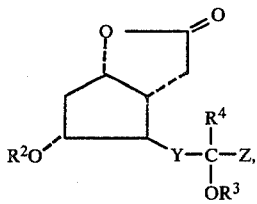

(III)

with a phosphorane of the general formula IX

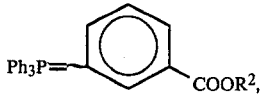

(IX)

in order to get a compound of the general formula I, wherein X is —CH$_2$— and converting optionally an obtained compound of the general formula I by halogen-hydrogen elimination, saponification, introducing or splitting off a protecting group, salt formation, esterification,
in order to get another compound of the general formula I.

The compounds of the general formulae II and III used as starting compounds are known or can be prepared by known methods by using suitable starting compounds [IL. Farmaco. Ed. Sc. 1976, 31, 763; IL. Farmaco 1972, 27, 1125; J. Org. Ch., 1981, 46, 1954–57; JACS, 1974, 96, 5865].

Phosphoranes of the general formula IX are preferably prepared from triphenyl-m-substituted-benzyl-phosphonium bromide, with a strong base, such as sodium methyl sulphonyl-methide /DIMSYL-Na/. The reaction and the further reaction of the obtained product is carried out preferably in anhydrous dimethyl sulfoxide.

When using as starting material a compound of the general formula II in the Wittig-reaction new PGF$_{2\alpha}$-derivatives of the general formula IV are obtained which can be isolated after acidification by extraction. When considering the 5,6-double bond of the formed product is a 1:1 mixture of E and Z isomers. The E and Z isomers can be easily separated by column chromatography. The thus obtained compounds per se possess a significant smooth muscle stimulating activity.

Unexpectedly upon the effect of the strong base, phosphorane the 14-halogen does not undergo an elimination leading to a 13,14-triple bond. At the same time elimination can be, if desired, carried out with alkoxide bases, such as potassium tert.butoxide or sodium tert. butoxide or sodium methoxide, or upon the effect of an excess of DIMSYL-Na.

If an elimination reaction is performed e.g. with an obtained PGF$_{2\alpha}$-derivative of the general formula VI

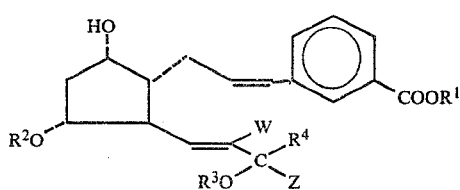

(VI)

then a 13,14-didehydro-PGF$_{2\alpha}$-derivative of the general formula VII

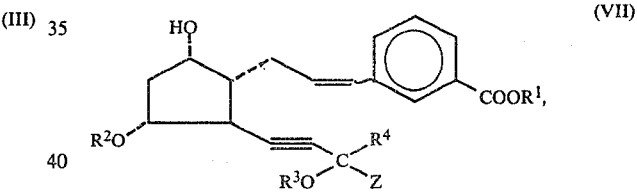

(VII)

is obtained.

The elimination reaction is conducted in a polar protic organic solvent, such as alcohols, preferably in an alcohol corresponding to the alcoholate or in aprotic solvents, such as tetrahydrofuran, dimethylsulfoxide etc.

The obtained compounds of the general formula IV can be converted to PGI$_1$ derivatives of the general formula V with an electrophilic agent of the general formula E-L by a method known in prostacycline chemistry /see JACS 1977, 2006/.

As electrophilic agents of the general formula E-L halogens, such as bromine or iodine /E=Br, I, L=Br, I/, or reactants giving electrophilic halonium /e.g. N-bromosuccinic imide/, complexes giving halogen /such as pyridinium bromide perbromide/, aryl selenyl derivatives /e.g. phenyl selenyl bromide, phenyl selenyl chloride/ and sulfenyl halides /e.g. phenyl selenyl chloride/ or N-halo-hydantoines may be used. In the cyclization reaction halogenated hydrocarbons, e.g. methylene chloride, chloroform or aprotic solvents, such as tetrahydrofuran, toluene can serve as medium. The raw products formed in the reaction may be employed without purification in the elimination reactions.

All the compounds of the general formula V are a mixture of exo- and endo-isomers according to position 6. The separation of the isomers may be performed by column chromatography, but the separation is not necessary as the mentioned elimination results in PGI$_2$ analogue of the general formula I in both cases.

No side reaction occurs as the elimination can take place only in one direction. The compounds of the general formula V can be converted to compounds of the general formula I by elimination reaction. The elimination may be performed by several methods according to the nature of E. If E stands for halogen than the elimination may be carried out with a suitable base. As bases alcoholates, such as potassium tert. botoxide, sodium ethylate, organic bases, such as 1,5-diazabicyclo[4,3,0]-non-5-ene /DBN/, 1,5-diazabicyclo[5,4,0]undec-5-ene /DBU/, pyridine, triethylamine or other strong conjugated bases, e.g. sodium methyl sulfinyl methide are preferred.

If E represents an iodine or bromine atom then potassium tert. butoxide, 1,5-diazabicyclo[4,3,0]non-5-ene or sodium methyl sulfinyl methide are preferred.

If E stands for phenyl selenyl or phenyl-thio then the elimination can be conducted by the following two methods:

One may oxidize Ph-S or PH-Se to the corresponding sulfone or selenone /E stands for

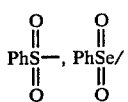

and eliminate same with the above mentioned base.

One may also prepare only sulfoxide or selenoxide /E stands for

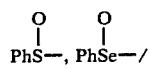

and the compounds of the general formula V are then subjected to thermal elimination.

When the desired product of the general formula I is a compound having —CH$_2$— group as X, then as starting material compounds of the general formula III are used /J. Org. Chem. 1981, 46, 1954/. The reaction of the compounds of the general formula III and phosphoranes of the general formula IX may be performed under same conditions as described for the reaction of the compounds of the general formula II with phosphoranes of the general formula IX. Compounds of the general formula I are directly obtained.

R$^1$, R$^2$ and R$^3$ in the obtained compounds of the general formula I can be split off after elimination separately or optionally simultaneously and can be exchanged for other groups R$^1$, R$^2$ and R$^3$.

For example if during the elimination a compound is obtained in which R$^1$ is methyl, R$^2$ and R$^3$ are hydrogen, then R$^2$ and R$^3$ may be replaced by acyl, such as acetyl, or acetal such as tetrahydro-pyranyl, or silyl, such as dimethyl tert. butyl silyl by chemical methods known per se.

When preparing an ester during the elimination and R$^1$ stands for methyl then in order to prepare a metal salt of the product one may proceed as follows: the methyl ester is hydrolysed with an alkali base, such as sodium hydroxide, potassium hydroxide, lithium hydroxide in a mixture of water-alcohol and then the reaction mixture is acidified. The formed acid is isolated by extraction and the desired salt is obtained by adding a calculated amount of lye in methanol.

The salts of the compounds of the general formula I are crystalline compounds.

Compounds containing —CH=CW— in place of Y may be converted to a derivative containing —C≡C— in place of Y at any stage of the reaction by method given for the intermediate of the general formula IV.

The term alkyl stands for C$_{1-6}$ alkyl groups, preferably methyl, ethyl, n- and iso-propyl, n-, iso-, sec.- and tert. butyl groups, various amyl and hexyl groups. The term alkenoyl represents groups of the general formula C$_n$H$_{2n+1}$—CO—, containing 1 to 6, preferably 1 to 4 carbon atoms, such as formyl, acetyl, propionyl and butyryl. The terms aryl and aryloxy stand for aromatic groups with one or two rings containing 6 to 10 carbon atoms. Latter groups may optionally be substituted by aryl, C$_{1-4}$ alkyl or alkoxy, halogen, trifluormethyl, or nitro, e.g. phenyl, chlorophenyl, trifluoromethylphenyl and the corresponding phenoxy and naphthyl groups. The acyl groups may be alkanoyl and aroyl groups. Examples of the aroyl groups are benzoyl or p-phenylbenzoyl.

The acetal type protecting groups may be for example tetrahydro pyranyl, 1-ethoxy-ethoxy and 1,4-dioxanyl. As silyl type protecting groups, preferably trialkyl silyl groups may be mentioned which have three same or different alkyl groups, e.g. dimethyl tert. butyl silyl.

Cations in place of R$^1$ may be metal or amine cations. All cations can be used which in the employed dosage do not possess any or only insignificant biological activity. As cations sodium, potassium, calcium, lithium, magnesium, further ammonium, and mono-, di-, tri- and tetra-substituted ammonium ions may be mentioned. The substituents may optionally favourably act upon the crystallization of the obtained salt or its processing. As cation e.g. tris-hydroxymethyl-methylammonium cation may be mentioned. The ammonium ions may be substituted by the alkyl groups given above.

The end product according to the invention may be employed in human and veterinary therapy in the form of pharmaceutical compositions for the inhibition of thrombocyte aggregation, as thrombolytic agents or for influencing the blood clotting. The pharmaceutical compositions contain one or more compounds of the invention in an efficient dosage and the pharmaceutically acceptable excipients, such as filling agents, diluents, pH-adjusting, osmotic pressure influencing and flavouring agents, and agents promoting flowability, tabletting, other formulation excipients, solvents, cosolvents etc.

The pharmaceutical compositions can be prepared in the form of tablets, dragées, powders, encapsulated powders, solutions /injectable and infusion solutions, fluid medicine, drops etc./, suppositories, and ointments. The most preferred forms are the tablets, dragées, and injectable or infusion solutions.

One dosage unit of the composition /tablet, dragée, injection vial/ contains preferably the dosage to be administered at once, or a part thereof e.g. the half of it or a multiple e.g. the double thereof.

As the compounds of the invention show similar biological activity as PGI$_2$, the dosage is also in the same range. The physician can differ from the known doses in both directions on the basis of his knowledge, considering the disorder to be treated and the desired effect. The doses can be increased all the more, that the compounds according to the invention show only 1/100–1/200 part of the undesired anti-hypertensive activity of PGI$_2$.

Further details of the invention can be found in the following Examples which serve only for illustration and not for limitation.

EXAMPLE 1

2,3,4-Trinor-1,5-inter-m-phenylene-14-bromo-20-methyl-PGF$_{2\alpha}$-methyl ester 722 mg. /30.2 mmoles/ of sodium hydride and 35 ml. of dry dimethyl sulfoxide are introduced under nitrogen atmosphere to a 100 ml. round bottomed flask. The suspension is stirred for 30 minutes at 65°–70° C. and for 30 minutes at 70°–75° C. The formed hydrogen gas is removed e.g. by a mercury seal bubble-maker. To the thus obtained solution 7.2 g. /15.1 mmoles/ of triphenyl-m-carboxy-benzyl-phosphonium bromide are added under nitrogen atmosphere.

The obtained suspension is stirred for 30 minutes at 35° C. The red viscous solution of the phosphorane thus obtained is added within 10 minutes at room temperature to a solution of 1.37 g. /3.77 mmoles/ of 3a$\beta$,4,5,6-,6a$\beta$-hexahydro-2-hydroxy-4$\beta$-[2-bromo-3/S/-hydroxy-1-nonenyl]-5$\alpha$-hydroxy-2H-cyclopenta/b/furan in 1 ml. of anhydrous tetrahydrofuran. The reaction mixture is stirred at 40° C. for 20 minutes.

The reaction mixture is then poured on a mixture of 100 ml. of water and 30 g. of ice and the pH is adjusted to 3–4 by adding 1N sulfuric acid solution. The solution is extracted with 4×30 ml. of ethyl acetate. The combined organic layers are extracted with 3×15 ml. of 1N sodium hydroxide solution. The combined alkaline extracts are adjusted to pH=3.5–4 by adding a 1N sulfuric acid solution and 80 ml. of diethyl ether and 10 ml. of 1 molar ethereal diazo-methane solution are added. The ether layer is separated, washed with saturated salt solution, dried and evaporated.

1.78 g. of raw product is obtained, which is chromatographed on silica gel column and eluted with a 3:1 mixture of ethyl acetate and benzene.

The fractions corresponding to 0.31 R$_f$ /on Merck silica gel plate Art 5715/ are collected in a system of 3:1 ethyl acetate and benzene and evaporated. 929 mg. /50%/ of end product are obtained.

Analysis of the product

Thin layer chromatography: R$_f$=0.31 /in 3:1 mixture of ethyl acetate:benzene/.

NMR /CDCl$_3$,$\delta$/: 7.3–8.1 /4H/; 6.2–6.7 /trans H-5, H-6 olephine protons/; 5.7–5.95 /cis-H5, H-6, H-13 olephine protons/; 4.0–4.35 /3H, H-9, H-11, H-15/; 3.92 /3H, methyl-ester CH$_3$/.

EXAMPLE 2

2,3,4-Trinor-1.5-inter-m-phenylene-13,14-didehydro-10-methyl-PGF$_{2\alpha}$-methyl ester 532 mg. /1.08 mmole/ of 2,3,4-trinor-1,5-inter-m-phenylene-14-bromo-20-methyl-PGF$_{2\alpha}$-methyl ester are dissolved in 12 ml. of abs. dimethyl sulfoxide, whereafter 1.22 g. /10.8 mmoles/ of potassium tert. butoxide is added. The obtained mixture is then stirred for 5 minutes and diluted with 20 ml. of saturated salt solution, 20 ml. of water and 80 ml. of ethyl acetate.

The aqueous layer is acidified with 1N sodium hydrogen sulphate to pH=3. The organic layer is separated, and the aqueous layer is extracted with 2×10 ml. of ethyl acetate. The organic layers are combined, cooled to 0° C. and treated with an ether solution of diazomethane /1M solution, 10–20 ml./.

The organic layer is dried on anhydrous sodium sulphate, the drying agent is filtered and the solvent is distilled off at reduced pressure. 474 mg. of raw product are obtained and chromatographed on silica gel column and eluted with a 3:1 mixture of ethyl acetate and benzene. The fractions corresponding to R$_f$=0.35 are collected, the solvent is distilled off at reduced pressure. Yield: 247 mg. /59.8%/.

Analytical Results

Thin layer chromatography: R$_f$=0.35 in 3:1 mixture of ethyl acetate and benzene.

NMR /CDCl$_3$,$\delta$/: 7.25–8.1 /4H, aromatic protons/; 6.3–6.58 /2H; H-5; H-6/; 4.0–4.5 /3H, H-9, H-11, H-15/; 3.95 /s, 3H, CH$_3$ ester /.

EXAMPLE 3

2,3,4-Trinor-1,5-inter-m-phenylene-5iodo-14-bromo-20-methyl-PGI$_1$-methyl ester 577 mg. /1.17 mmole/ of 2,3,4,-trinor-1,5-inter-m-phenylene-14-bromo-20 -methyl-PGF$_{2\alpha}$-methyl ester are dissolved in 2 ml. of methylene-chloride and under stirring 11.6 ml. /11.6 mmoles/ of 1 mmole/ml. concentrated sodium hydrogen carbonate solution is added.

To the reaction mixture of two layers 23.4 ml. /2.34 mmoles/ of a 0.1 mmole/ml methylene chloride iodine solution are added. The reaction mixture is vigorously stirred for 1 hour at room temperature, diluted with 100 ml. of ethyl acetate and the excess iodine is removed with a 5% sodium thiosulphate solution. The organic layer is separated and the aqueous part is extracted with 2×15 ml. of ethyl acetate. The organic layers are collected and washed with saturated salt solution, dried above anhydrous sodium sulphate, filtered and the solvent is distilled off at reduced pressure.

Yield: 720 mg.

Analysis

Thin layer chromatography: R$_f$=0.6 and 0.65. developed twice in a 3:1 system of ethyl acetate and benzene.

EXAMPLE 4

2,3,4-Trinor-1,5-inter-m-phenylene-5-iodo-13,14-didehydro-20-methyl-PGI$_1$-methyl ester One may proceed as disclosed in Example 3 but as starting material 483 mg. /1.17 mmole/ of 2,3,4-trinor-1,5-inter-m-phenylene-13,14 -didehydro-20-methyl-PGF$_{2\alpha}$-methyl ester are used.

Yield: 603 mg.

Analysis

Thin layer chromatography: R$_f$=0.67 and 0.60 /in a 3:1 mixture of ethyl acetate and benzene/.

EXAMPLE 5

2,3,4-Trinor-1,5-inter-m-phenylene-14-bromo-20-methyl-PGI$_2$-methyl ester 689 mg. /1.11 mmole/ of 2,3,4-trinor-1,5-inter-m-phenylene-5-iodo-14-bromo-20-methyl-PGI$_1$-methyl ester are added into a 10 ml. round-bottomed flask. The air space of the flask is several times rinsed with nitrogen gas. 1 ml. of 1.5-diazabicyclo[4,3,C]-non-5-ene is added under inert gas atmosphere. The obtained mixture is then stirred for 2 hours at 40° C. and then cooled to room temperature, diluted with 50 ml. ether and the ether layer is washed with 3×5 ml. of water. The ether layer is dried above anhydrous sodium sulphate, filtered and evaporated at reduced pressure.

543 mg. of raw product are obtained, and chromatographed on silica gel column, and eluted with a 5:1 mixture of dichloroemethane and acetone. $R_f$=0.73 and 0.69. The corresponding fractions are collected and evaporated separately.

The product having $R_f$=0.73 corresponds to a 5,6/Z/ geometrical isomer containing a double bond.
Yield: 216 mg. /39.5%/.

The product having $R_f$=0.69 corresponds to a 5,6/E/-geometrical isomer containing a double bond.
Yield: 206 mg. L/37.7%/.

Analysis

Thin layer chromatography: $R_f$=0.73 and 0.69 /on Merck silica gel plate—Art 5715—developed twice in a 3:1 mixture of dichloromethane and acetone.

NMR /CDCl$_3\delta$/: 7.3–8.2 /m, 4H, aromatic protons/; 5.85 /d, 1H, H-19/; 5.3 /s, 1H, H-5/; 4.83 /m, 1H, H-9/; 3.95–4.2 /m, 2H, H-11, H-15/; 3.94 /s, 3H, CH$_3$ ester/.

EXAMPLE 6

2,3,4-Trinor-1,5-m-phenylene-13,14-didehydro-20-methyl-PGI$_2$-methyl ester

One proceeds according to Example 5 but as starting material 599 mg. /1.11 mmole/ of 2,3,4-trinor-1,5-inter-m-phenylene-5-iodo-13,14-didehydro-20-methyl-PGI$_1$-methyl ester are used.
Yield: 218 mg. /52.8%/.

Analysis

Thin layer chromatography: Rf$_2$=0.50 in a 3:1 mixture of benzene and ethyl acetate.

NMR /CDCl$_3\delta$/: 7.3–8.1 /m, 4H, aromatic protons/; 5.95 and 5.3 /s, 1H, E or Z H-5/; 4.05–4.5 /2H, H-11and H-15/; 4.75 /dt, 1H, H-9/; 4.95 /3H, CH$_3$ ester/.

EXAMPLE 7

2,3,4-Trinor-1,5-inter-m-phenylene-13,14-didehydro-20-methyl-PGI$_2$-methyl ester 494 mg. /1 mmole/ of 2,3,4-trinor-1,5-inter-m-phenylene-14-bromo-20-methyl-PGI$_2$-methyl ester are dissolved in 5 ml. of abs. dimethyl sulfoxide. 550 mg. /5mmoles/ of potassium tert. butoxide are added to the solution at room temperature. The suspension is stirred for 5–10 minutes, diluted with 50 ml. of water and the pH of the obtained aqueous solution is adjusted to 4 by adding 1N oxylic acid solution and the mixture is then extracted with 30+20+20 ml. of ethylacetate of 0° C. The organic layers are combined, dried above anhydrous sodium sulphate, filtered and the solution is treated with 10 ml. 1 Mol/1 ether-diazomethane solution at 0° C. The solvent is distilled off at reduced pressure and the raw product is chromatographed on silica gel column in a 5:1 mixture of dichloromethane and acetone. Fractions having $R_f$=0.50 are collected in 3:1 mixture of benzene:ethylacetate and are evaporated at reduced pressure. 255.6 mg. /62%/ of the title product are obtained.

Analysis is the same as given in Example 6.

If the process according to the Example is employed for the 5,6/Z/ product prepared as disclosed in the Example as starting material, then the 5/Z/ isomer of the title compound is obtained as a product. If the same process is employed for the 5,6/E/ product prepared as given in Example 5 as starting material then as a product the 5/E/ isomer of the title compound is obtained.

EXAMPLE 8

2,3,4-Trinor-1,5-inter-m-phenylene-14-bromo-20-methyl-PGI$_2$ sodium salt 988 mg. /2mmoles/ of 2,3,4-trinor-1,5-inter-m-phenylene 14-bromo-20-methyl-PGI$_2$ methyl ester are dissolved in 1 ml. methanol. 1 ml. /10 mmoles/ of 5N aqueous sodium hydroxide solution is added at room temperature. The reaction mixture is stirred at room temperature for 1 hour. Methanol is then distilled off at reduced pressure and 10 ml. of an 1:1 mixture of saturated salt solution and water are added to the residue and the solution is extracted with 3×5 ml. ether. The aqueous layer is cooled to 0° C., whereafter 20 ml. of ethyl acetate are added and the pH of the mixture is adjusted to 4–4.5 under vigorous stirring. The layers are then separated and the aqueous layer is extracted with 3×5 ml. of ethyl acetate. The organic layers are combined, dried above anhydrous sodium sulphate, filtered and evaporated. 841 mg. of raw acid are obtained, this acid is then dissolved in 0.5 ml. of methanol and to the obtained solution. 1.75 ml. of a methanolic solution of 1N sodium hydroxide is added. Methanol is removed by distillation at reduced pressure. The obtained raw product is suspended in 1 ml. abs. tetrahydrofuran and filtered.
Yield: 878.5 mg. /87.5%/.

Analysis

Thin layer chromatography: $R_f$=0.54 /on Merck silica gel plate—Art 5715 in a 20:20:1 mixture of benzene:dioxane:acetic acid/.

EXAMPLE 10

2,3,4-Trinor-1,5-inter-m-phenylene-20-methyl-13,14-didehydro-6a-carbaprostaglandin-I$_2$-methyl ester 20 mmoles of sodium methyl sulfinyl methide are dissolved in 20 ml. of dimethylsulfoxide (prepared from 480 mg. of sodium hydride and 20 ml. of abs. sulfoxide). The solution is cooled to 15°–20° C. and 4.77 g. (10 mmoles) of triphenyl-3-carboxy-benzyl-phosphonium bromide are added. The formed red solution is stirred for 30 minutes at 35° C. and cooled to room temperature. 1.34 g. (3 mmoles) of 7α-(tetrahydropyrane-2-yl-oxy)-6β-[3s-(tetrahydropyrane-2-yl-oxy)-1-noninyl]-bicyclo[3,3,0]-octane-3-one dissolved in 1 ml. abs. tetrahydrofuran is added. The reaction mixture is stirred at 40° C. for 48 hours, cooled to room temperature. 10 ml. of water are added and the pH of the solution is adjusted to neutral by adding 1N sodium hydrogen sulphate, and the solution is extracted with 3×20 ml. of ethyl acetate. The organic extracts are combined and washed with 3×10 ml. of water and 1×10 ml. of saturated salt solution, dried above anhydrous sodium sulphate and filtered. The solution is cooled to 0° C. and treated with 10 ml. of a 1 mmole/ml ether diazomethane solution and the solvent is distilled off at reduced pressure and the obtained raw product (2 g.) is chromatographed on silica gel column with a 4:1 mixture of benzene and ethyl acetate.

Fractions corresponding to $R_f$-values 0.48 and 0.43 are collected (after developing in a 3:1 mixture of benzene and ethyl acetate) and evaporated at reduced pressure.

Yield: 644.5 mg. (37%) of 5/Z/ isomer $R_f=0.48$
Yield: 679.3 mg. (39%) of 5/E/ isomer $R_f=0.43$.

The obtained fractions are dissolved separately in a 3:1:1.5 mixture of acetic acid-water-tetrahydrofuran and stirred at 45° C. for 3 hours. The reaction mixture is cooled to room temperature and 40 ml. of a saturated salt solution and 40 ml. of ethyl acetate are added. The organic layer is separated, the aqueous layer is extracted with 2×5 ml. of ethyl acetate. The organic layers are combined and washed to neutral with 2×10 ml. of saturated sodium hydrogen carbonate solution. The organic layer is dried above anhydrous sodium sulphate, filtered and the solvent is evaporated at reduced pressure. The raw product is chromatographed on silica gel column with ethyl acetate.

Yield: 380.4 mg. (31.9%) of 5/Z/ and 387.6 mg (32.5%) of 5/E/ isomers. ($R_f=0.28$ and 0.25 in ethyl acetate.)

Analysis

Thin layer chromatography: $R_f=0.28$ and 0.25 resp. (on Merck silica gel plate=Art 1715—in ethyl acetate).

NMR (CDCl$_3\delta$): 7.25–8.0 (4H); 5.6 (1H); 3.5–4.25 (5H).

EXAMPLE 11

2,3,4-Trinor-1,5-inter-m-phenylene-20-methyl-13,14-didehydro-6a-carbaprostaglandine-I$_2$ sodium salt One may proceed according to Example 8 but as starting material 385.6 mg. (0.97 mmole) of 2,3,4-trinor-1,5-inter-m-phenylene-20-methyl-13,14-didehydro-6a-carba-prostaglandin-I$_2$-methyl ester are used.

Yield: 352.8 mg. (87%).

Analysis

Thin layer chromatography: $R_f=0.6$ (on Merck silica gel plate—Art 5715 in a 20:10:1 mixture of benzene-dioxan-acetic acid).

According to the process given in Examples 1 to 11 the following compounds are prepared from the appropriate starting materials:

2,3,4-trinor-1,5-inter-m-phenylene-13,14-didehydro-20-ethyl-PGI$_2$ sodium salt ($R_f=0.57$) in a 20:10:1 system of benzene-dioxan-acetic acid on Merck silica gel plate Art 5719), 2,3,4,17,18,19,20-heptanor-1,3-inter-m-phenylene-13,14-didehydro-16-phenoxy-PGI$_2$ sodium salt, $R_f=0.6$ (in the above system), 2,3,4,17,18,19,20-heptanor-1,5-inter-m-phenylene-13,14-didehydro-16-(3-trifluormethyl-phenoxy)-PGI$_2$ sodium salt $R_f=0.62$ (in the above system), 2,3,4-trinor-1,5-inter-m-phenylene-14-bromo-20-ethyl-PGI$_2$ sodium salt $R_f=0.57$ (in the above system), 2,3,4,17,18,19,20-heptanor-1,5-inter-m-phenylene-16-phenyl-13,14-didehydro-PGI$_2$ sodium salt $R_f=0.69$ (in the above system), 2,3,4-trinor-1,5-inter-m-phenylene-11,15-bis(tetrahydropyran-2-yl-oxy)-13,14-didehydro-20-methyl-PGI$_2$ methyl ester, $R_f=0.87$ (in a 3:1 mixture of benzene and ethyl acetate).

2,3,4-trinor-1,5-inter-m-phenylene-11,15-bis(dimethyl-tert.butyl-silyloxy)-13,14-didehydro-20-methyl-PGI$_2$-methyl ester, $R_f=0195$ (in a 3:1 mixture of benzene and ethyl acetate).

We claim:

1. A compound of the formula I

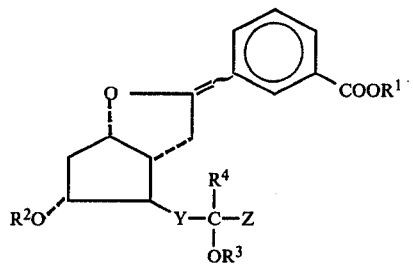

wherein

R$^1$ is hydrogen, C$_1$ to C$_4$ alkyl, or a pharmaceutically acceptable primary, secondary, tertiary, or quaternary ammonium cation, or a pharmaceutically acceptable metal cation, R$^2$ and R$^3$ are each independently hydrogen, C$_1$ to C$_6$ alkanoyl, benzoyl, p-phenyl-benzoyl, tetrahydropyranyl, 1-ethoxy-ethoxy, 1,4 dioxanyl, or an alkylsilyl-protecting group, R$^4$ is hydrogen or C$_1$ to C$_4$ alkyl, Y is —C≡C— or a trans —CH=CW— group, wherein W is chloro, bromo or fluoro, and Z is n-hexyl or n-heptyl or Z is phenylmethyl, naphthylmethyl, phenoxymethyl, or naphthyloxymethyl, each of which is unsubstituted or substituted by C$_1$ to C$_4$ alkyl, C$_1$ to C$_4$ alkoxy, halogen, trifluoromethyl, nitro, phenyl, or naphthyl.

2. The compound of the formula I defined in claim 1 wherein Y is a trans —CH=CW— group, wherein W is chloro, bromo or fluoro.

3. The compound of the formula I defined in claim 1 wherein Z is n-hexyl or n-heptyl.

4. The compound of the formula I defined in claim 2 wherein Z is n-hexyl or n-heptyl.

5. 2,3,4-Trinor-1,5-inter-m-phenylene-14-bromo-20-methyl-PGI$_2$-methylester as defined in claim 1.

6. 2,3,4-Trinor-1,5-inter-m-phenylene-13,14-didehydro-20-methyl-PGI$_2$-methylester as defined in claim 1.

7. 2,3,4-Trinor-1,5-inter-m-phenylene-14-bromo-20-methyl-PGI$_2$-sodium salt as defined in claim 1.

8. 2,3,4-Trinor-1,5-inter-m-phenylene-13,14-didehydro-20-methyl-PGI$_2$-sodium salt as defined in claim 1.

9. 2,3,4-Trinor-1,5-inter-m-phenylene-13,14-didehydro-20-ethyl-PGI$_2$-sodium salt as defined in claim 1.

10. 2,3,4-Trinor-1,5-inter-m-phenylene-14-bromo-20-ethyl-PGI$_2$-sodium salt as defined in claim 1.

11. 2,3,4,17,18,19,20-Heptanor-1,5-inter-m-phenylene-13,14-didehydro-16-phenoxy-PGI$_2$-sodium salt as defined in claim 1.

12. 2,3,4,17,18,19,20-Heptanor-1,5-inter-m-phenylene-13,14-didehydro-16-(3-trifluoromethyl-phenoxy)-PGI$_2$-sodium salt as defined in claim 1.

13. 2,3,4,17,18,19,20-Heptanor-1,5-inter-m-phenylene-13,14-didehydro-16-phenyl-PGI$_2$-sodium salt as defined in claim 1.

14. 2,3,4-Trinor-1,5-inter-m-phenylene-11,15-bis(tetrahydropyran-2-yl-oxy)-13,14-didehydro-20-methyl-PGI$_2$-methyl-ester as defined in claim 1.

15. 2,3,4-Trinor-1,5-inter-m-phenylene-11,15-bis(-dimethyl-tert.butyl-silyl-oxy)-13,14-didehydro-20-methyl-PGI$_2$-methylester as defined in claim 1.

16. A method of inhibiting blood platelet aggregation which comprises the step of administering to a subject in need thereof a pharmaceutically effective amount of the compound of the Formula (I) defined in claim 1.

* * * * *